United States Patent [19]

Bergthaller et al.

[11] Patent Number: 5,021,332
[45] Date of Patent: Jun. 4, 1991

[54] COLOR PHOTOGRAPHIC RECORDING MATERIAL CONTAINING A DIR COUPLER

[75] Inventors: Peter Bergthaller, Bergisch Gladbach; Thomas Krüger, Leverkusen; Hans Vetter, Cologne; Heinrich Odenwälder, Leverkusen, all of Fed. Rep. of Germany

[73] Assignee: Agfa Gevaert Aktiengesellschaft, Leverkusen, Fed. Rep. of Germany

[21] Appl. No.: 528,045

[22] Filed: May 23, 1990

[30] Foreign Application Priority Data

Jun. 6, 1989 [DE] Fed. Rep. of Germany ....... 3918395

[51] Int. Cl.$^5$ .............................. G03C 7/36
[52] U.S. Cl. .................. 430/544; 430/557; 430/957
[58] Field of Search ................ 430/557, 544, 957

[56] References Cited

U.S. PATENT DOCUMENTS

| | | | |
|---|---|---|---|
| 3,227,554 | 1/1966 | Barr et al. | 430/557 |
| 3,617,291 | 11/1971 | Sawdey | 430/544 |
| 4,201,584 | 5/1980 | Monbaliu et al. | 430/389 |
| 4,510,234 | 4/1985 | Matsuzaka et al. | 430/557 |
| 4,870,000 | 9/1989 | Bergthaller et al. | 430/544 |

*Primary Examiner*—Richard L. Schilling
*Attorney, Agent, or Firm*—Connolly and Hutz

[57] ABSTRACT

Good edge effects and inter-image effects are obtained where DIR couplers corresponding to formula I are used in color photogrpahic silver halide materials.

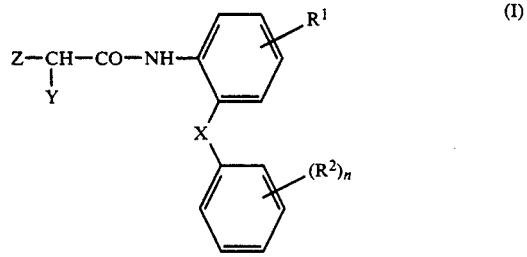

in which
R$^1$ is H, Cl, —CF$_3$, alkoxy, sulfamoyl;
R$^2$ is H, Cl, alkyl, cycloalkyl, alkoxy, alkoxycarbonyl, carbamoyl;
n is 0, 1 or 2;
X is O or S;
Y is a group with a silver halide development inhibiting function releasable during color development;
Z is benzoyl, pivaloyl, carbamoyl or a quinazolin-4-on-2-yl group.

5 Claims, No Drawings

COLOR PHOTOGRAPHIC RECORDING MATERIAL CONTAINING A DIR COUPLER

This invention relates to a color photographic recording material comprising at least one photosensitive silver halide emulsion layer containing a coupler which releases a development inhibitor during color development.

It is known that chromogenic development can be carried out in the presence of compounds which, during development, release substances that are capable of diffusing to form an image and of developing a certain effect, for example influencing the development of silver halide. If this effect is that further development is inhibited, compounds of the type in question are called DIR (development inhibitor releasing) compounds. The DIR compounds may be of the type which react with the oxidation product of a color developer to form a dye with elimination of an inhibitor group (DIR couplers) or of the type which release the inhibitor without at the same time forming a dye. Compounds of the latter type are also called DIR compounds in the narrower sense.

DIR couplers are known, for example, from U.S. Pat. No. 3,148,062, U.S. Pat. No. 3,227,554, U.S. Pat. No. 3,615,506, U.S. Pat. No. 3,617,291 and DE-A-24 14 006.

The development inhibitors released are generally heterocyclic mercapto compounds or derivatives of benzotriazole. DIR couplers which release monocyclic triazoles as development inhibitor are described, for example, in DE-A-28 42 063 and in DE-A-0 272 573. A number of photographic effects influencing image quality can be obtained by using DIR compounds. Such effects include, for example, the reduction of gradation, the formation of a finer color grain, the improvement of definition by the so-called edge effect and the improvement of color purity and color brilliance by so-called inter-image effects, cf. for example the Article entitled "Development-Inhibitor-Releasing (DIR) Couplers in Color Photography" by C. R. Barr, J. R. Thirtle and P. W. Vittum in Photographic Science and Engineering 13, 74 (1969).

DIR compounds which couple without dye formation have the advantage over DIR couplers which couple with dye formation that they can be universally used so that the same compound may be used in all photosensitive layers of a color photographic recording material irrespective of the color to be produced. By contrast, on account of the color produced from them, DIR couplers can generally only be used in some of the photosensitive layers unless the secondary color density attributable to them can be tolerated in the other layers. This advantage of DIR compounds is offset by the disadvantage that they are generally less reactive than DIR couplers. In practice, therefore, DIR couplers only are used, two or more different DIR couplers being used where necessary in the same recording material. Different DIR couplers may be associated with the differently spectrally sensitized layers according to the color produced from them.

It is normally important that the development inhibitor be rapidly released from the coupler during development because it is intended to influence the further course of the development process. Accordingly, it is highly desirable that the couplers in question show high activity. Highly active DIR couplers are described, for example, in EP-A-0 287 833.

The problem addressed by the present invention is to provide a color photographic recording material containing DIR couplers with a silver halide development inhibitor attached to the coupling position, from which the inhibitor is rapidly released during development.

The present invention relates to a color photographic recording material comprising at least one photosensitive silver halide emulsion layer and a DIR coupler associated therewith, characterized in that the coupler corresponds to formula I:

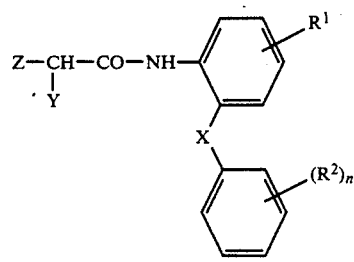

in which
$R^1$ is H, Cl, —$CF_3$, alkoxy, sulfamoyl;
$R^2$ is H, Cl, alkyl, cycloalkyl, alkoxy, alkoxycarbonyl, carbamoyl;
n is 0, 1 or 2;
X is O or S;
Y is a group releasable during color development with a silver halide development inhibiting function;
Z is benzoyl, pivaloyl, carbamoyl or a quinazolin-4-on-2-yl group.

An alkoxy radical represented by $R^1$ in formula I may contain for example up to 16 carbon atoms. A sulfamoyl group represented by $R^1$ may be substituted once or twice, for example by alkyl, cycloalkyl, aralkyl or aryl; two such substituents, together with the nitrogen atom, may also form a 5- or 6-membered ring.

An alkyl radical represented by $R^2$ in formula I contains, for example, from 1 to 10 carbon atoms. An alkoxy radical represented by $R^2$ contains, for example, up to 16 carbon atoms. An alkoxycarbonyl radical represented by $R^2$ contains, for example, up to 17 carbon atoms. A carbamoyl group represented by $R^2$ has the same definition as the sulfamoyl group $R^1$.

A cycloalkyl radical represented by $R^2$ or present in $R^1$ or $R^2$ in formula I is preferably cyclohexyl.

A benzoyl group represented by Z in formula I may be substituted, for example by alkoxy, preferably in the p-position. A carbamoyl group represented by Z in formula I is preferably derived from phenyl carbamic acid, in which the phenyl ring may be substituted, for example, by Cl, alkoxycarbonyl and/or a group

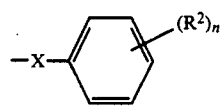

in which X, $R^2$ and n are as already defined.

A quinazolin-4-on-2-yl group represented by Z in formula I may be substituted, for example by Cl or acylamino.

The group with a silver halide development inhibiting function represented by Y in formula I corresponds to the following formula A—(TIME)$_n$—INH in which INH is a silver halide development inhibitor, n is 0 or 1 and the binding link represented by TIME is a group which, after release from the coupling position of the coupler during its coupling with the oxidation product of the silver halide developer, is capable of releasing the inhibitor attached thereto in a following reaction. The group TIME is also called a timing group because, where a group such as this is present, the inhibitor attached thereto is in many cases released and can become active with delay. Known timing groups include, for example, a group

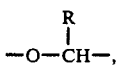

where the O atom is attached to the coupling position of the coupler while the C atom is attached to an N atom of an inhibitor (for example DE-A-27 03 145), a group which undergoes an intramolecular nucleophilic displacement reaction after release from the coupler and, in the process, releases the inhibitor (for example DE-A-28 55 697), a group in which, after release from the coupler, an electron transfer can take place along a conjugated system, resulting in release of the inhibitor (for example DE-A-31 05 026), or the group $$-X-\overset{\overset{\displaystyle NR}{\|}}{C}-,$$

where X (for example —O—) is attached to the coupling position of the coupler and the C atom is attached to an atom of the inhibitor and in which R represents aryl for example (for example EP-A-0 127 063).

The TIME group may be present or even completely absent (where n=0).

DIR couplers corresponding to formula I, in which Z is a quinazolin-4-on-2-yl group, are preferred and, among these DIR couplers, those in which $R^2$ is an o-cyclohexyl group are preferred.

Preferred silver halide development inhibitors (Y or INH) are those of the 1,2,3-triazole or 1,2,4-triazole series.

The following are examples of DIR couplers according to the invention:

DIR-1

DIR-2

DIR-3

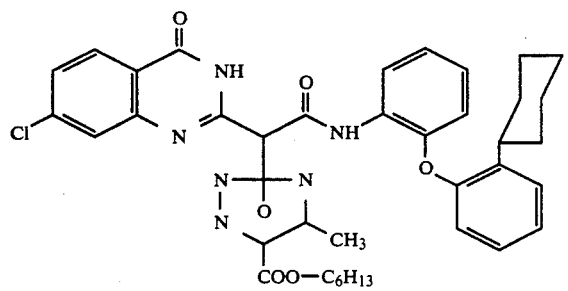
DIR-4
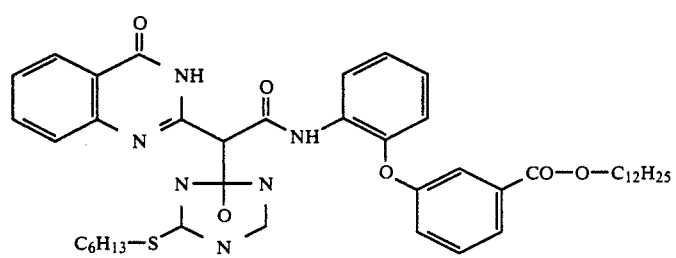
DIR-5
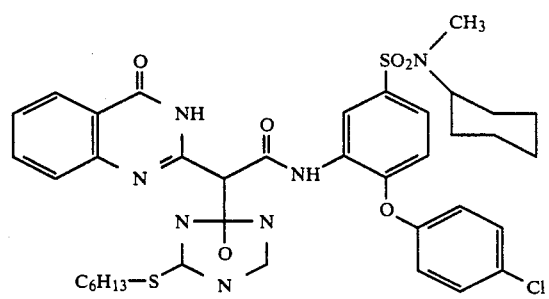
DIR-6
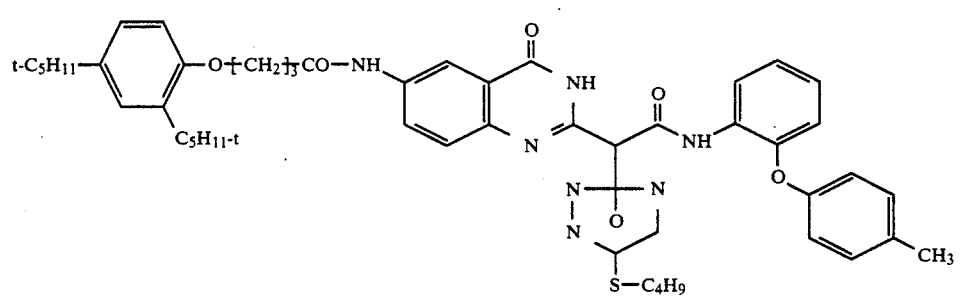
DIR-7
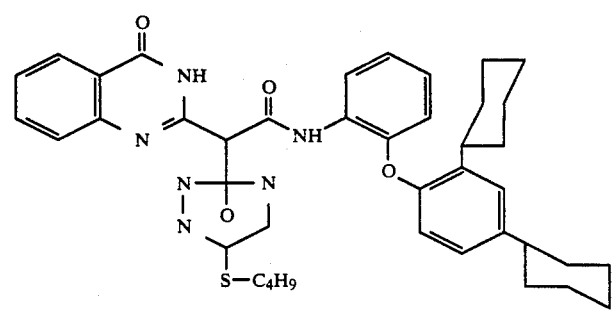
DIR-8

-continued
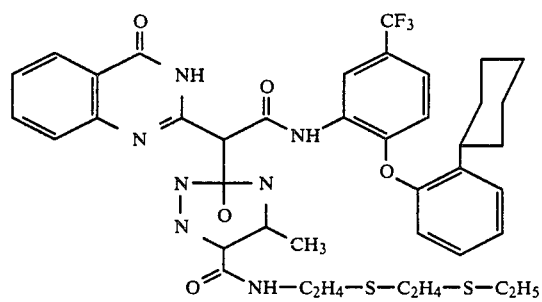
DIR-9
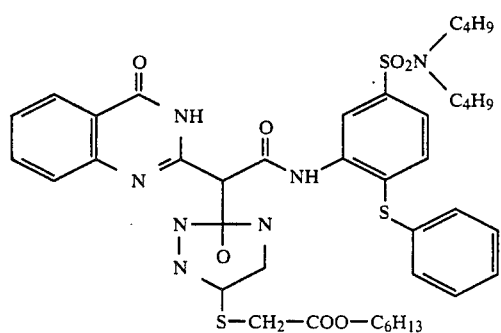
DIR-10
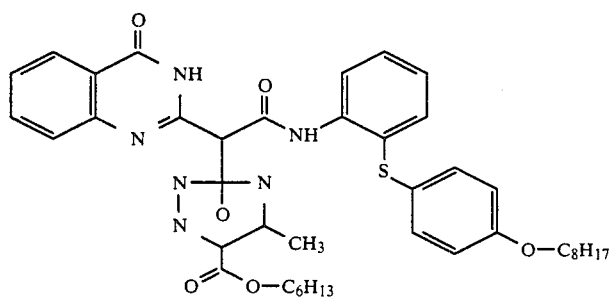
DIR-11
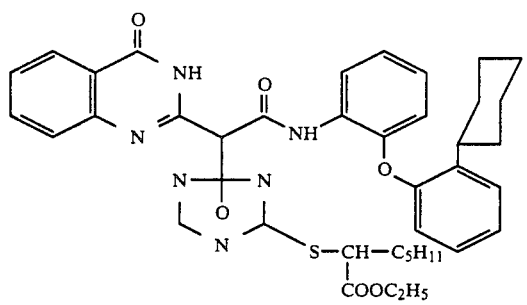
DIR-12
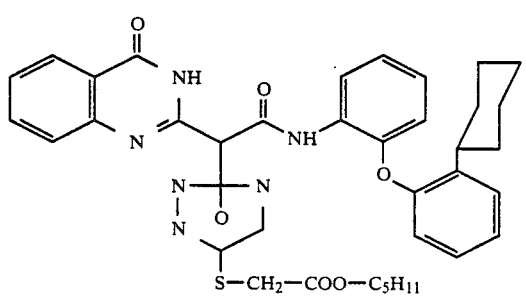
DIR-13

-continued

DIR-14

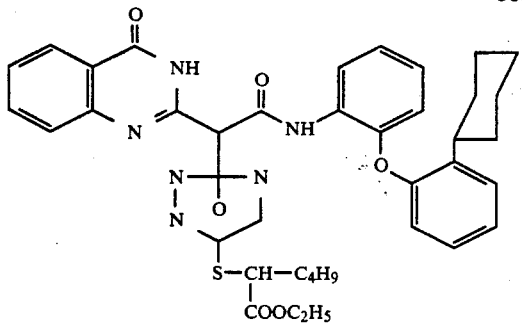

Preparation Example 1
DIR coupler DIR-1

1. 2-Cyanacetamido-2'-cyclohexyl diphenyl ether A solution of 103 g dicyclohexyl carbodiimide in 200 ml dichloromethane is added dropwise at 30° to 40° C. to a solution of 45 g cyanoacetic acid (anhydrous) and 140 g 2-amino-2'-cyclohexyl diphenyl ether, prepared by reaction of 2-chloronitrobenzene with 2-cyclohexyl phenol potassium in dimethyl sulfoxide and subsequent hydrogenation, in 1,000 ml dichloromethane. After refluxing for 1 hour, the reaction mixture is cooled to 20° C. and the dicyclohexyl urea precipitated is filtered off under suction. The filter residue is washed with 400 ml dichloromethane at 40° C., the combined filtrates are concentrated by evaporation and the residue is recrystallized from ethyl acetate. Yield: 240 g (72% of the theoretical), Mp.: 179°-80° C.

2. After addition of 23 g ethanol, a suspension of 100 g 2-cyanacetamino-2'-cyclohexyl diphenyl ether in 1,000 ml ethyl acetate is saturated with HCl gas with cooling to 0°-5° C. After standing for 16 hours, the suspension is concentrated in vacuo at room temperature to half its volume, filtered under suction and the residue washed with 100 ml ethyl acetate. Yield: 97.5 g (78% of theoretical) Melting point: 104° C. with decomposition. The imino ether hydrochloride obtained is added in portions with stirring to a solution heated to 85° C. of 33 g 2-aminobenzamide in 140 ml ethanol. The reaction mixture is refluxed with stirring to 2 h and poured onto 250 g ice. Crystallization occurs during standing overnight. The mother liquor is decanted off and recrystallized from acetonitrile: Yield: 65 g (60% of the theoretical) Melting point: 197°-200° C.

3. 3,4-Dihydro-4-oxoquinazolin-2-bromoacetic acid 2-(2-cyclohexyl)-phenoxyanilide A suspension of 45.3 g of the coupler obtained in 2. is brominated in 200 ml acetic acid by addition of 16 g bromine in 80 ml acetic acid at 25° to 30° C. After stirring for 1 hour at 25° C., the suspension is introduced into 500 ml ice water and 10 g sodium acetate. After standing overnight, the supernatant solution is decanted off and the residue is digested with methanol and filtered under suction. Yield: 50 g Melting point: 180° C. (decomposition)

4. 6 g potassium carbonate are introduced with stirring into a solution of 10.65 g of the brominated coupler from 3. and 4.5 g 5-methyl-1,2,3-triazole carboxylic acid n-hexyl ester in 150 ml ethyl acetate. After stirring for a total of 4 h at 25° to 30° C., the mixture is poured onto 400 ml water and 5 ml acetic acid, the ethyl acetate phase is separated off, dried with sodium sulfate and concentrated by evaporation in vacuo. The red-brown oil obtained crystallizes out over 24 h on stirring with ethanol. Yield: 8.4 g Melting point: 176°-178° C. The compound consists of two isomers; the major quantity consists of a relatively weakly polar isomer melting at 172° to 173° C., the minor quantity consists of a high-melting isomer (Mp. 217° C.).

All the DIR couplers according to the invention are characterized by an o-aryloxy or o-arylthio substitution in the ballast anilide part. They are highly active DIR couplers, the corresponding DIR couplers of the quinazolone acetanilide series in particular showing increased reactivity in relation to all other ballast anilide structures tested and, hence, greater inhibition and higher interimage effects and edge effects. This is reflected in an improvement in color reproduction and sharpness and possibly even in improved grain.

The compounds according to the invention are suitable for use as DIR couplers in color photographic, more especially multilayer recording materials. Where they are yellow couplers, they are preferably used in, or in association with, a photosensitive silver halide emulsion layer predominantly sensitive to the blue spectral region of visible light. The particular advantage of the couplers according to the invention, namely the comparatively low inhibition of development in the layer with which such a compound is associated in addition to the comparatively high inhibition of development in adjacent, non-associated layers, is of course particularly relevant in the case of a multilayer color photographic recording material which, in addition to a predominantly blue-sensitive silver halide emulsion layer, contains other photosensitive silver halide emulsion layers predominantly sensitive to the green or red spectral region of visible light.

Couplers which produce very little color during development may be associated as required with a blue-sensitive layer, a green-sensitive layer or a red-sensitive layer or even with several of these layers without any danger of color falsification.

By virtue of their extremely high activity, the DIR couplers according to the invention may also be used in comparatively small quantities as color couplers to produce the desired effects, particularly the inter-image effects. For example, this enables a yellow DIR coupler according to the invention to be used not only in the blue-sensitive layers producing yellow dye, but also in other layers without an excessive, unwanted secondary density occurring in those layers. Accordingly, the DIR couplers according to the invention may also be advantageously used as yellow couplers in magenta layers and in cyan layers.

In the production of the photosensitive photographic recording material, the non-diffusing DIR couplers according to the invention may be incorporated in the casting solution of the silver halide emulsion layers or other colloid layers in known manner, optionally together with other couplers. For example, oil-soluble or hydrophobic couplers may be added to a hydrophilic colloid solution, preferably from a solution in a suitable coupler solvent (oil former), optionally in the presence of a wetting agent or dispersant. In addition to the binder, the hydrophilic casting solution may of course contain other typical additives. The solution of the coupler need not be directly dispersed in the casting solution for the silver halide emulsion layer or any other water-permeable layer; instead, it may advantageously first be dispersed in an aqueous non-photosensitive solution of a hydrophilic colloid and the mixture obtained, optionally after removal of the low-boiling organic solvent used, may be mixed with the casting solution for the photosensitive silver halide emulsion layer or any other water-permeable layer before application.

Suitable photosensitive silver halide emulsions are emulsions of silver chloride, silver bromide or mixtures thereof, optionally with a small content of silver iodide of up to 20 mol-%, in one of the hydrophilic binders typically used. Gelatine is preferably used as binder for the photographic layers, although it may be completely or partly replaced by other natural or synthetic binders.

The emulsions may be chemically and spectrally sensitized in the usual way and the emulsion layers and other non-photosensitive layers may be hardened in the usual way with known hardeners.

Color photographic recording materials typically contain at least one silver halide emulsion layer for recording light of each of the three spectral regions red, green and blue. To this end, the photosensitive layers are spectrally sensitized in known manner by suitable sensitizing dyes. Blue-sensitive silver halide emulsion layers do not necessarily have to contain a spectral sensitizer because, in many cases, the natural sensitivity of the silver halide is sufficient for recording blue light.

Each of the photosensitive layers mentioned may consist of a single layer or, in known manner, for example as in the so-called double layer arrangement, may also comprise two or even more partial silver halide emulsion layers (DE-C-1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present, they may be arranged immediately adjacent one another or in such a way that a photosensitive layer of different spectral sensitivity is present between them (DE-A-1 958 709, DE-A-25 30 645, DE-A-26 22 922).

Color photographic recording materials for the production of multicolor images normally contain dye-producing compounds, in the present case particularly color couplers, for producing the cyan, magenta and yellow dye images in spatial and spectral association with the silver halide emulsion layers of different spectral sensitivity.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally non-photosensitive binder layer.

By spectral association it is meant that the spectral sensitivity of each of the photosensitive silver halide emulsion layers and the color of the component dye image produced from the particular spatially associated color coupler bear a certain relationship to one another, a component dye image relating to another color (for example the colors cyan, magenta or yellow) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same. They are merely required to produce at least substantially the same color during color development, normally a color which is complementary to the color of the light to which the silver halide emulsion layers in question are predominantly sensitive.

In preferred embodiments, at least one non-diffusing color coupler for producing the cyan component dye image is associated with red-sensitive silver halide emulsion layers, at least one non-diffusing color coupler for producing the magenta component dye image is associated with green-sensitive silver halide emulsion layers and at least one non-diffusing color coupler for producing the yellow component dye image is associated with blue-sensitive silver halide emulsion layers.

However, other associations are also possible.

Color couplers for producing the cyan dye image are generally couplers of the phenol or α-naphthol type, of which suitable examples are:

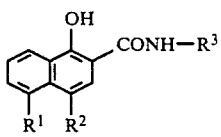

C-1: $R^1$, $R^2$ = H; $R^3$ = 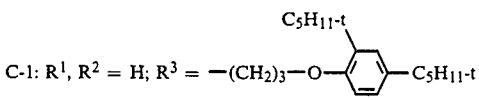

C-2: $R^1$ = $-NHCOOCH_2-CH(CH_3)_2$; $R^2$ = H;
 $R^3$ = $-(CH_2)_3-OC_{12}H_{25}$
C-3: $R^1$ = H; $R^2$ = $-OCH_2-CH_2-SO_2CH_3$; $R^3$ = $-C_{16}H_{33}$
C-4: $R^1$ = H; $R^2$ = $-OCH_2-CONH-(CH_2)_2-OCH_3$;
 $R^3$ = 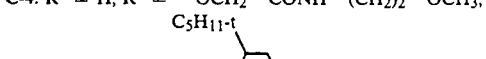

C-5: $R^1$, $R^2$ = H; $R^3$ = 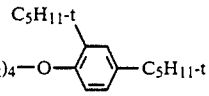

C-6: $R^1, R^2 = H$; $R^3 = -(CH_2)_4-O-$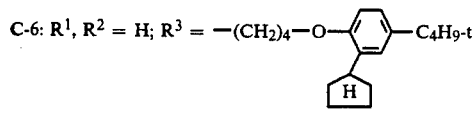

C-7: $R^1 = H$; $R^2 = Cl$; $R^3 = -C(C_2H_5)_2-C_{21}H_{43}$
C-8: $R^1 = H$; $R^2 = -O-CH_2-CH_2-S-CH(COOH)-C_{12}H_{25}$
$R^3 = $ Cyclohexyl

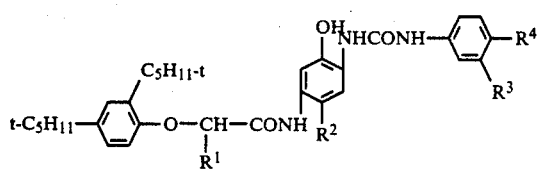

C-9: $R^1 = -C_4H_9$; $R^2 = H$; $R^3 = -CN$; $R^4 = Cl$
C-10: $R^1 = -C_4H_9$; $R^2 = H$; $R^3 = H$; $R^4 = -SO_2CHF_2$
C-11: $R^1 = -C_4H_9$;
$R^2 = -O-$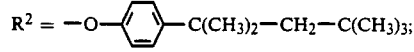$-C(CH_3)_2-CH_2-C(CH_3)_3$;
$R^3 = H$; $R^4 = -CN$ C-12: $R^1 = C_2H_5$; $R^2, R^3 = H$; $R^4 = -SO_2CH_3$
C-13: $R^1 = -C_4H_9$; $R^2, R^3 = H$; $R^4 = -SO_2-C_4H_9$
C-14: $R^1 = -C_4H_9$; $R^2 = H$; $R^3 = -CN$; $R^4 = -CN$
C-15: $R^1 = -C_4H_9$; $R^2, R^3 = H$; $R^4 = -SO_2-CH_2-CHF_2$
C-16: $R^1 = -C_2H_5$; $R^2, R^3 = H$; $R^4 = -SO_2CH_2-CHF-C_3H_7$
C-17: $R^1 = -C_4H_9$; $R^2, R^3 = H$; $R^4 = F$
C-18: $R^1 = -C_4H_9$; $R^2, R^3 = H$; $R^4 = -SO_2CH_3$

C-19: $R^1 = -C_4H_9$; $R^2, R^3 = H$; $R^4 = -CN$

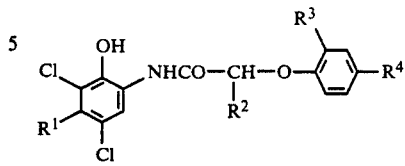

C-20: $R^1 = -CH_3$; $R^2 = -C_2H_5$; $R^3, R^4 = -C_5H_{11}$-t
C-21: $R^1 = -CH_3$; $R^2 = H$; $R^3, R^4 = -C_5H_{11}$-t
C-22: $R^1, R^2 = -C_2H_5$; $R^3, R^4 = -C_5H_{11}$-t
C-23: $R^1 = -C_2H_5$; $R^2 = -C_4H_9$; $R^3, R^4 = -C_5H_{11}$-t
C-24: $R^1 = -C_2H_5$; $R^2 = -C_4H_9$; $R^3, R^4 = C_4H_9$-t

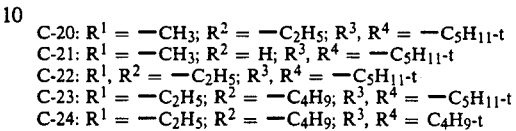

C-25: $R^1, R^2 = -C_5H_{11}$-t; $R^3 = -C_4H_9$; $R^4 = H$; $R^5 = -C_3F_7$
C-26: $R^1 = -NHSO_2-C_4H_9$; $R^2 = H$; $R^3 = -C_{12}H_{25}$; $R^4 = Cl$;
$R^5 = $ phenyl
C-27: $R^1, R^2 = -C_5H_{11}$-t; $R^2 = Cl$, $R^3 = -C_3H_7$-i; $R^4 = Cl$;
$R^5 = $ pentafluorophenyl
C-28: $R^1 = -C_5H_{11}$-t; $R^2 = Cl$; $R^3 = -C_6H_{13}$; $R^4 = Cl$;
$R^5 = $ -2-chlorophenyl Color couplers for producing the magenta dye image are generally couplers of the 5-pyrazolone, indazolone or pyrazoloazole type, of which suitable examples are:

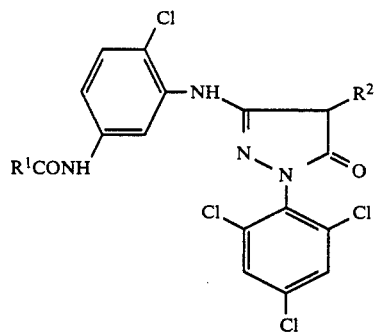

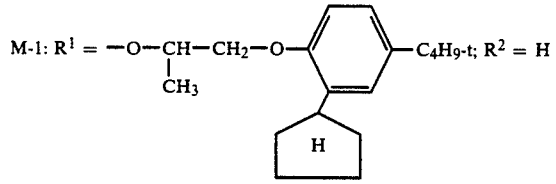

M-1: $R^1 = -O-CH-CH_2-O-$<image>-$C_4H_9$-t; $R^2 = H$
         $|$
         $CH_3$

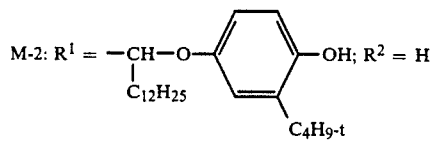

M-2: $R^1 = -CH-O-$<image>-OH; $R^2 = H$
         $|$
         $C_{12}H_{25}$         $C_4H_9$-t

M-3: $R^1 = -C_{13}H_{27}$; $R^2 = H$
M-4: $R^1 = -OC_{16}H_{33}$; $R^2 = H$

-continued
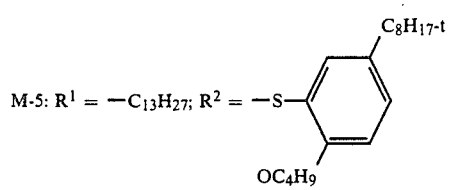
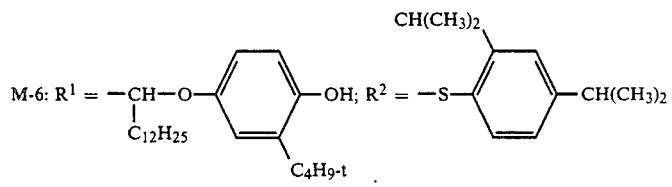
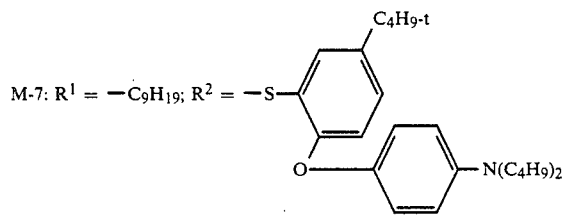
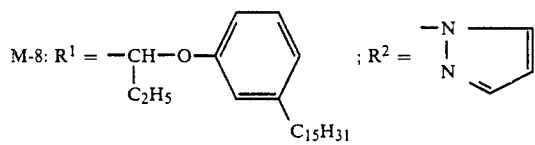
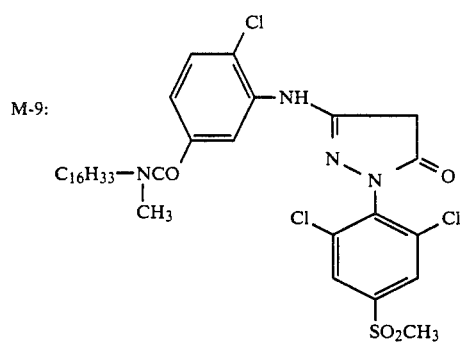
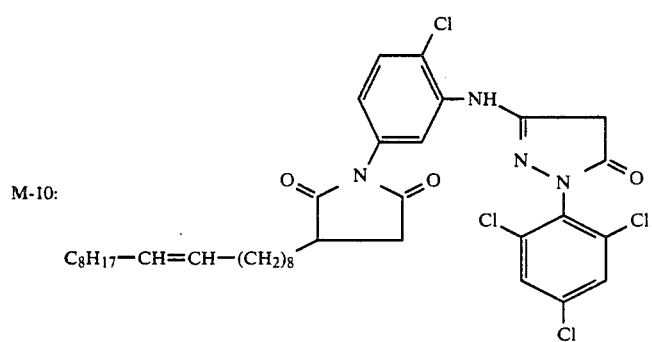

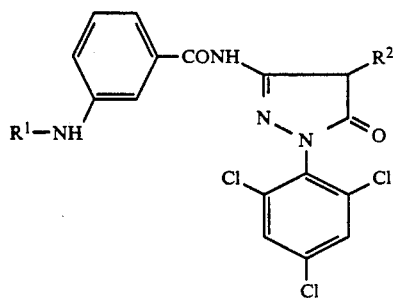
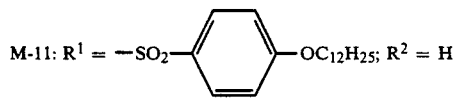
M-11: $R^1 = -SO_2-\phantom{}$—OC$_{12}$H$_{25}$; $R^2 = H$
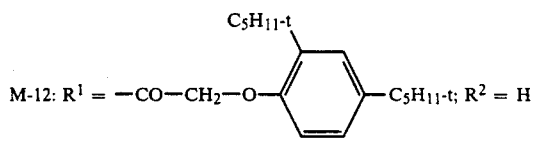
M-12: $R^1 = -CO-CH_2-O-\phantom{}$ ; $R^2 = H$
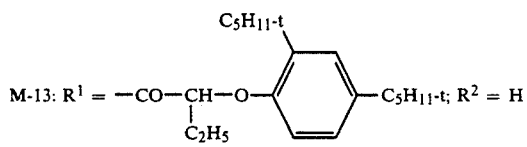
M-13: $R^1 = -CO-CH-O-\phantom{}$ ; $R^2 = H$
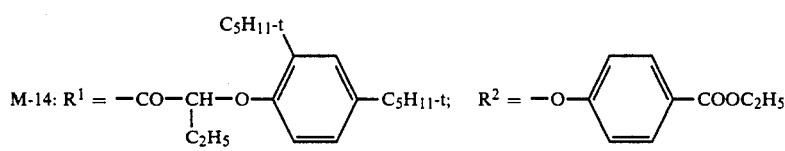
M-14: $R^1 = -CO-CH-O-\phantom{}$ ; $R^2 = -O-\phantom{}$—COOC$_2$H$_5$
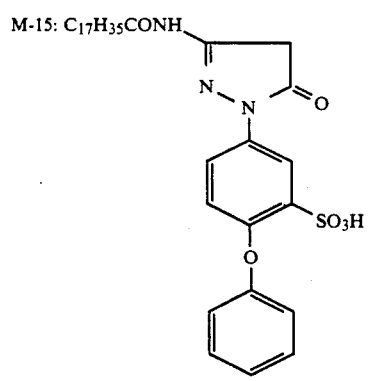
M-15:
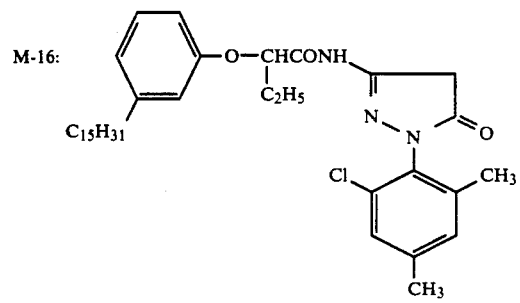
M-16:

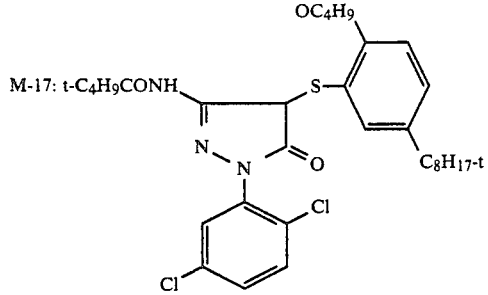

M-17:

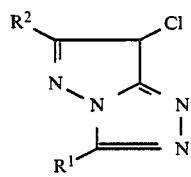

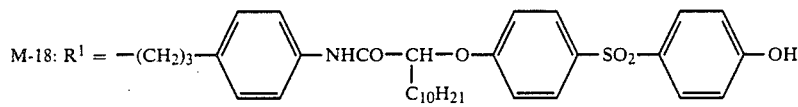

M-18: $R^1 = -(CH_2)_3-$ ... ; $R^2 = -CH_3$

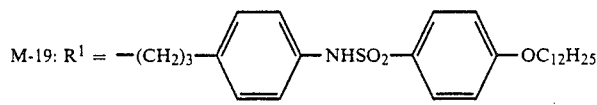

M-19: $R^1 = -(CH_2)_3-$ ... ; $R^2 = -CH_3$

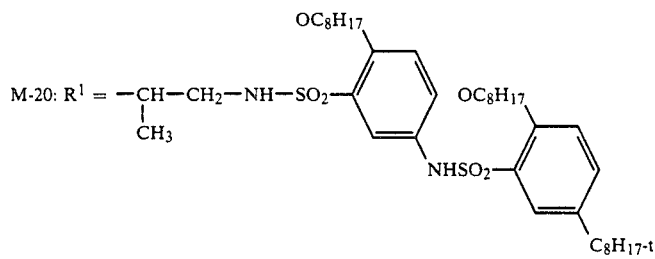

M-20: $R^1 = -CH-CH_2-NH-SO_2-$ ... ; $R^2 = -C_4H_9\text{-}t$

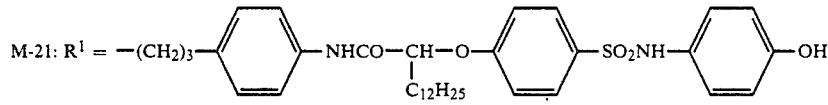

M-21: $R^1 = -(CH_2)_3-$ ... ; $R^2 = -CH_3$

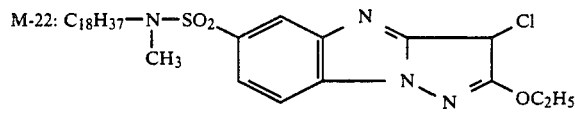

M-22:

Color couplers for producing the yellow component dye image are generally couplers containing an open-chain ketomethylene group, more especially couplers of the α-acetyl acetamide type, of which suitable examples are α-benzoyl acetanilide couplers and α-pivaloyl acetanilide couplers corresponding to the following formulae:

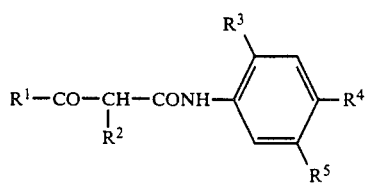

-continued

Y-1: $R^1 = -C_4H_9\text{-}t$; $R^2 =$ 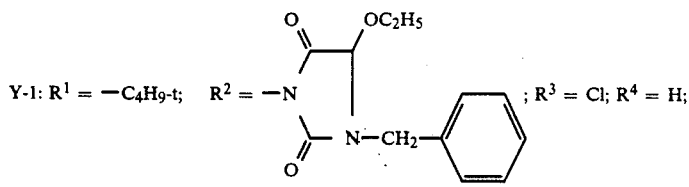 ; $R^3 = Cl$; $R^4 = H$;

$R^5 =$ 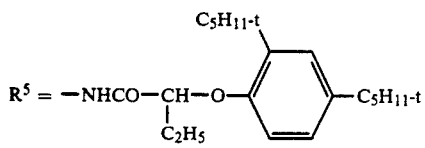

Y-2: $R^1 = -C_4H_9\text{-}t$; $R^2 =$ 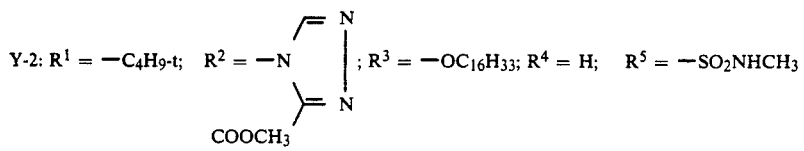 ; $R^3 = -OC_{16}H_{33}$; $R^4 = H$; $R^5 = -SO_2NHCH_3$ Y-3: $R^1 = -C_4H_9\text{-}t$; $R^2 =$ 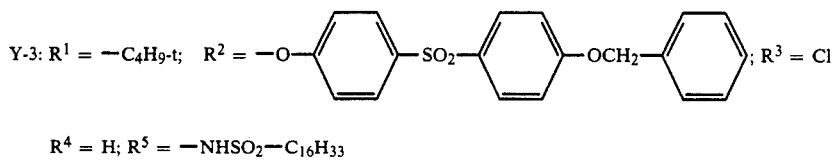 ; $R^3 = Cl$ $R^4 = H$; $R^5 = -NHSO_2-C_{16}H_{33}$ Y-4: $R^1 = -C_4H_9\text{-}t$; $R^2 =$ 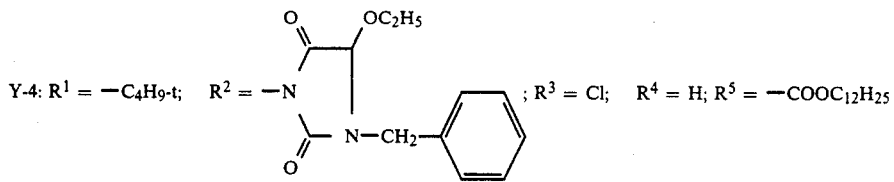 ; $R^3 = Cl$; $R^4 = H$; $R^5 = -COOC_{12}H_{25}$ Y-5: $R^1 = -C_4H_9\text{-}t$; $R^2 =$ 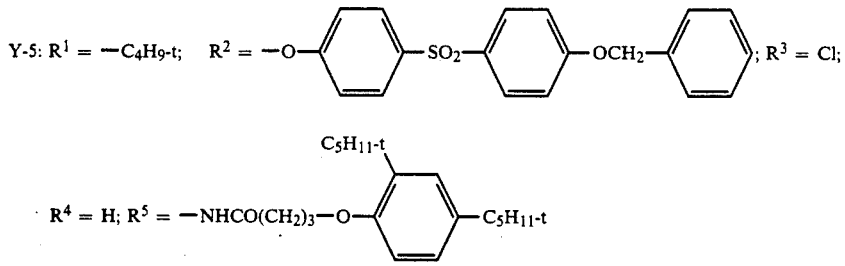 ; $R^3 = Cl$;

$R^4 = H$; $R^5 =$ 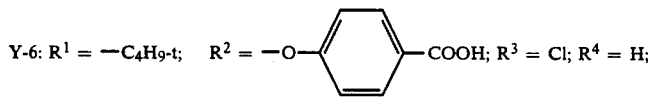

Y-6: $R^1 = -C_4H_9\text{-}t$; $R^2 =$ 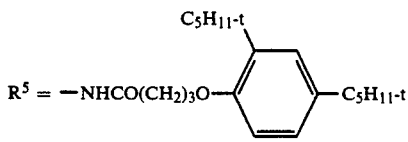—COOH; $R^3 = Cl$; $R^4 = H$;

$R^5 =$ 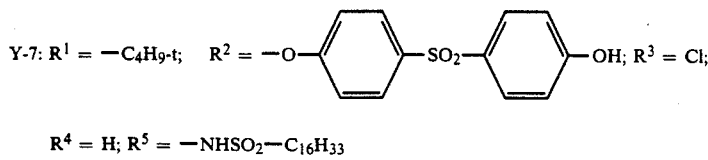

Y-7: $R^1 = -C_4H_9\text{-}t$; $R^2 = -O-$⟨phenyl⟩$-SO_2-$⟨phenyl⟩$-OH$; $R^3 = Cl$;

$R^4 = H$; $R^5 = -NHSO_2-C_{16}H_{33}$

Y-8: $R^1 = -C_4H_9\text{-}t$; $R^2 = $ 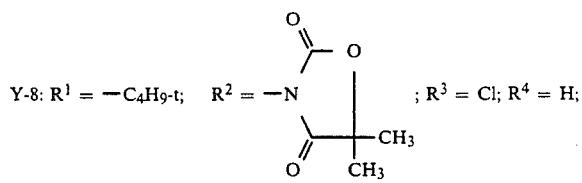 ; $R^3 = Cl$; $R^4 = H$;
$R^5 = $ 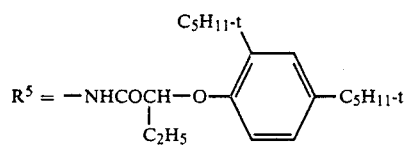
Y-9: $R^1 = -C_4H_9\text{-}t$; $R^2 = $ 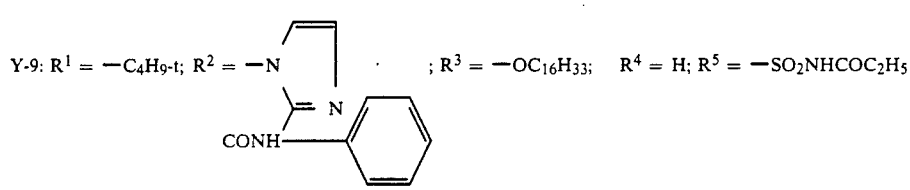 ; $R^3 = -OC_{16}H_{33}$; $R^4 = H$; $R^5 = -SO_2NHCOC_2H_5$
Y-10: $R^1 = -C_4H_9\text{-}t$; $R^2 = $ 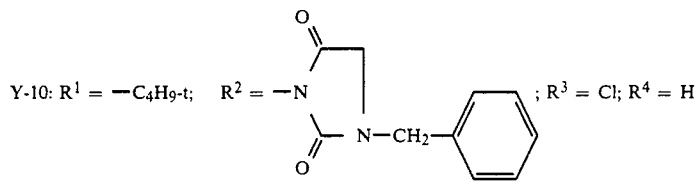 ; $R^3 = Cl$; $R^4 = H$
$R_3 = $ 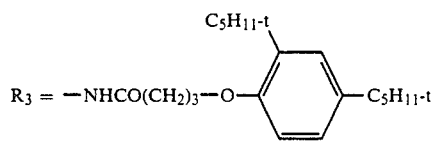
Y-11: $R^1 = -C_4H_9\text{-}t$; $R^2 = $ 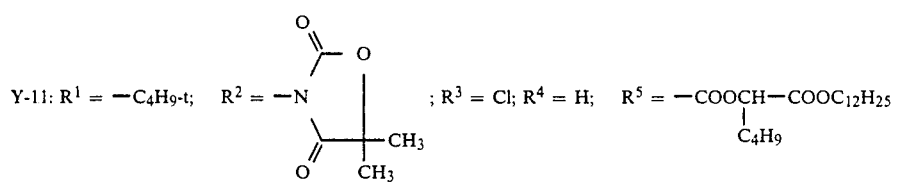 ; $R^3 = Cl$; $R^4 = H$; $R^5 = -COOCH(C_4H_9)-COOC_{12}H_{25}$
Y-12: $R^1 = -C_4H_9\text{-}t$; $R^2 = $ 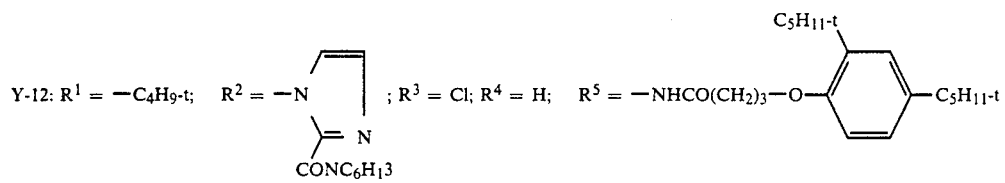 ; $R^3 = Cl$; $R^4 = H$; $R^5 = $ —NHCO(CH$_2$)$_3$—O—(2-$C_5H_{11}$-t, 4-$C_5H_{11}$-t-phenyl)
Y-13: $R^1 = -C_4H_9\text{-}t$; $R^2 = $ 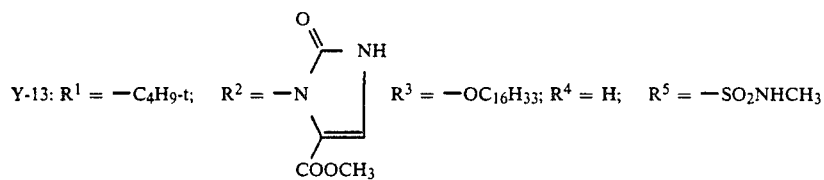 $R^3 = -OC_{16}H_{33}$; $R^4 = H$; $R^5 = -SO_2NHCH_3$
$R_3 = $ 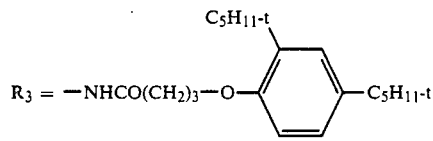

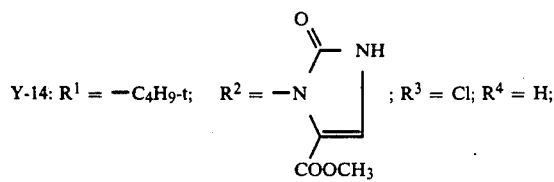

Y-14: $R^1 = -C_4H_9\text{-}t$; $R^2 = $ (structure shown); $R^3 = Cl$; $R^4 = H$;

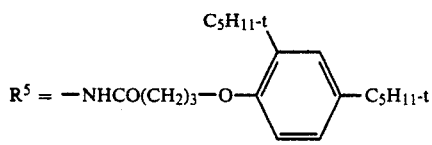

$R^5 = -NHCO(CH_2)_3-O-$ (structure shown)

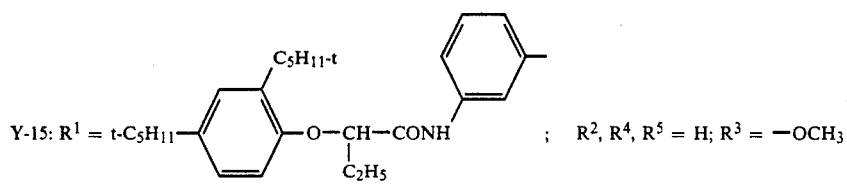

Y-15: $R^1 = t\text{-}C_5H_{11}$ (structure shown); $R^2, R^4, R^5 = H$; $R^3 = -OCH_3$

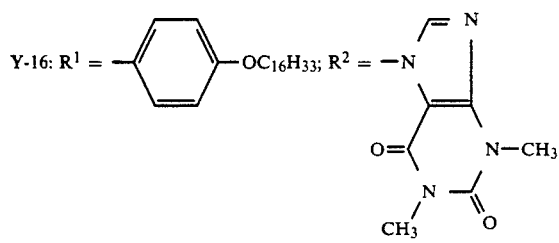

Y-16: $R^1 = $ —⟨phenyl⟩—$OC_{16}H_{33}$; $R^2 = $ (structure shown)

$R^3, R^5 = -OCH_3$; $R^4 = H$

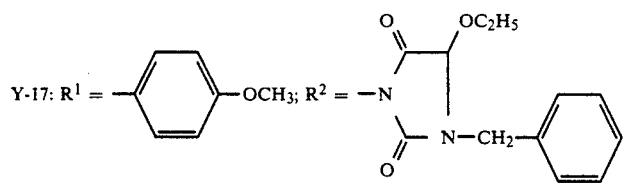

Y-17: $R^1 = $ —⟨phenyl⟩—$OCH_3$; $R^2 = $ (structure shown)

$R^3 = Cl$; $R^4 = H$; $R^5 = -COOC_{12}H_{25}$

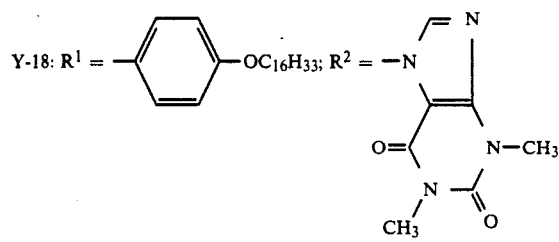

Y-18: $R^1 = $ —⟨phenyl⟩—$OC_{16}H_{33}$; $R^2 = $ (structure shown)

$R^3 = Cl$; $R^4, R^5 = -OCH_3$

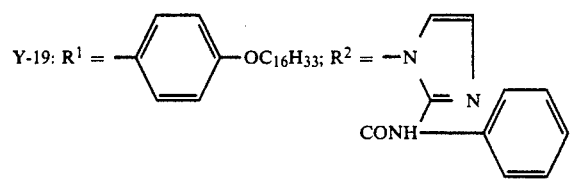

Y-19: $R^1 = $ —⟨phenyl⟩—$OC_{16}H_{33}$; $R^2 = $ (structure shown)

$R^3 = -OCH_3$; $R^4 = H$; $R^5 = -SO_2N(CH_3)_2$

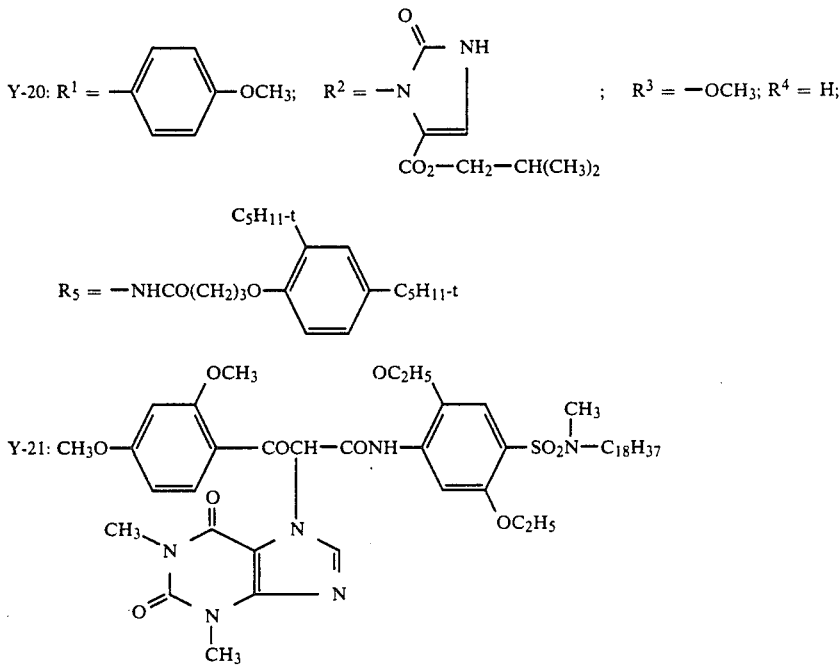

The color couplers may be 4-equivalent couplers also 2-equivalent couplers. 2-Equivalent couplers are derived from 4-equivalent couplers in that they contain in the coupling position a substituent which is eliminated during the coupling reaction. 2-Equivalent couplers include those which are colorless and also those which have a strong color of their own that either disappears during the color coupling reaction or is replaced by the color of the image dye produced (mask couplers) and also white couplers which produce substantially colorless products on reaction with color developer oxidation products. 2-Equivalent couplers also include couplers which contain in the coupling position a releasable group which is released on reaction with color developer oxidation products and develops a certain desirable photographic activity, for example as a development inhibitor or accelerator, either directly or after one or more further groups have been released from the group initially released (cf. for example DE-A-27 03 145, DE-A-28 55 697, DE-A-31 05 026, DE-A-33 19 428). Examples of 2-equivalent couplers such as these are the known DIR couplers and also DAR and FAR couplers.

Since, in the case of DIR, DAR and FAR couplers, it is primarily the activity of the group released during the coupling reaction which is desirable, the dye-producing properties of these couplers being less important, it is also possible to use DIR, DAR and FAR couplers which produce substantially colorless products during the coupling reaction (DE-A-1 547 640).

The releasable group may also be a ballast group so that coupling products which are diffusible or which at least show weak or limited mobility are obtained during the reaction with color developer oxidation products (U.S. Pat. No. 4,420,556).

According to the invention, the color photographic recording material additionally contains at least one DIR coupler corresponding to formula I which may be arranged not only in the yellow layer, but also in the magenta layer and/or even in the cyan layer and even in a non-photosensitive layer adjacent one of the layers mentioned.

In addition to the constituents mentioned above, the color photographic recording material according to the invention may contain other additives, such as for example antioxidants, dye stabilizers and agents for influencing the mechanical and electrostatic properties. In order to reduce or avoid the adverse effect of UV light on the dye images produced with the color photographic recording material according to the invention, it is of advantage for example to use UV absorbers in one or more of the layers present in the recording material, preferably in one of the upper layers. Suitable UV absorbers are described, for example, in U.S. Pat. No. 3,253,921, in DE-C-2 036 719 and in EP-A-0 057 160.

The usual layer supports may be used for the materials according to the invention, cf. Research Disclosure No. 17 643, Chapter XVII.

Suitable protective colloids or binders for the layers of the recording material are the usual hydrophilic film formers, for example proteins, particularly gelatine. Casting aids and plasticizers may be used, cf. the compounds mentioned in Research Disclosure No. 17 643, Chapters IX, XI and XII.

The layers of the photographic material may be hardened in the usual way, for example with hardeners of the epoxide type, the heterocylic ethylene imine type and the acryloyl type. It is also possible to harden the layers by the process according to DE-A-22 18 009 to obtain color photographic materials suitable for high-temperature processing. The photographic layers may also be hardened with hardeners of the diazine, triazine or 1,2-dihydroquinoline series or with hardeners of the vinyl sulfone type. Other suitable hardeners are known from DE-A-24 39 551, DE-A-22 25 230, DE-A-23 17 672 and from the above-cited Research Disclosure 17 643, Chapter XI.

Other suitable additives can be found in Research Disclosure 17 643 and in "Product Licensing Index", December, 1971, pages 107–110.

To produce color photographic images, the color photographic recording material according to the invention is developed with a color developer compound. Suitable color developer compounds are any developer compounds which are capable of reacting with color couplers in the form of their oxidation product to form azomethine dyes. Suitable color developer compounds are aromatic compounds containing at least one primary amino group of the p-phenylenediamine type, for example N,N-dialkyl-p-phenylenediamines, such as N,N-diethyl-p-phenylenediamine, 1-(N-ethyl-N-methylsulfonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine.

Other useful color developers are described, for example, in J. Amer. Chem. Soc. 73, 3100 (1951) and in G. Haist, Modern Photographic Processing, 1979, John Wiley and Sons, New York, pages 545 et seq.

After color development, the material is bleached and fixed in the usual way. Bleaching and fixing may be carried out separately or even together with one another. Suitable bleaches are any of the usual compounds, for example $Fe^{3+}$ salts and $Fe^{3+}$ complex salts, such as ferricyanides, dichromates, water-soluble cobalt complexes, etc. Particular preference is attributed to iron(III) complexes of aminopolycarboxylic acids, more especially for example ethylenediamine tetraacetic acid, N-hydroxyethyl ethylenediamine triacetic acid, alkyliminodicarboxylic acids and of corresponding phosphonic acids. Persulfates are also suitable bleaches.

EXAMPLE 1

A color photographic recording material for color negative development was prepared (layer combination 1 A-comparison) by application of the following layers in the order indicated to a transparent layer support of cellulose triacetate. The quantities are all based on 1 m². For the silver halide applied, the corresponding quantities of $AgNO_3$ are shown. All the silver halide emulsions were stabilized with 0.1 g 4-hydroxy-6-methyl-1,3,3a,7-tetraazaindene per 100 g $AgNO_3$.

Layer combination 1 A (comparison)

Layer 1 (anti-halo layer)
black colloidal silver sol containing
0.2 g Ag
1.2 g gelatine
0.1 g UV absorber UV-1
0.2 g UV absorber UV-2
0.02 g tricresyl phosphate (TCP)
0.03 g dibutyl phthalate (DBP)
Layer 2 (micrate intermediate layer)
micrate silver bromide iodide emulsion (0.5 mol-% iodide; mean grain diameter 0.07 μm) of 0.25 g $AgNO_3$ containing
1.0 g gelatine
Layer 3 (red-sensitized layer, medium sensitivity)
red-sensitized silver bromide iodide emulsion
(4.0 mol-% iodide; mean grain diameter 0.45 μm)
5.35 g $AgNO_3$ containing
3.75 g gelatine
1.33 g cyan coupler C-19
0.05 g red mask RM-1
0.118 g DIR coupler DIR-A
1.33 g TCP
0.236 g DBP
Layer 4 (intermediate layer)
of 1.43 g gelatine
0.74 g scavenger
Layer 5 (green-sensitized layer, medium sensitivity)
green-sensitized silver bromide iodide emulsion
(4.0 mol-% iodide; mean grain diameter 0.45 μm)
of 3.10 g $AgNO_3$ containing
2.33 g gelatine
0.775 g magenta coupler M-12
0.050 g yellow mask YM-1
0.068 g DIR coupler DIR-A
0.775 g TCP
0.136 g DBP
Layer 6 (intermediate layer)
as layer 4
Layer 7 (yellow filter layer)
yellow colloidal silver sol containing
0.09 g Ag
0.34 g gelatine
Layer 8 (blue-sensitive layer, medium sensitivity)
blue-sensitized silver bromide iodide emulsion
(4.0 mol-% iodide; mean grain diameter 0.45 μm)
of 3.46 g $AgNO_3$ containing
1.73 g gelatine
1.25 g yellow coupler Y-20
0.076 g DIR coupler DIR-A
1.25 g TCP
0.152 g DBP
Layer 9 (intermediate layer)
as layer 4
10 (protective and hardening layer)
of 0.68 g gelatine
0.73 g hardener (CAS Reg. No. 65411-60-1)
0.50 g formaldehyde scavenger FF.

In addition to the couplers already mentioned, the following compounds are used in Example 1:

UV absorber UV-1

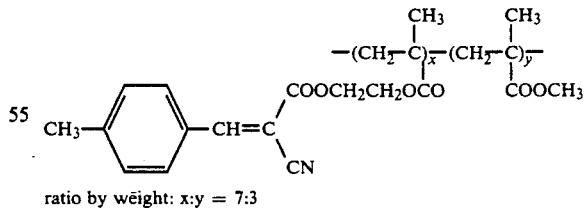

ratio by weight: x:y = 7:3

UV absorber UV-2

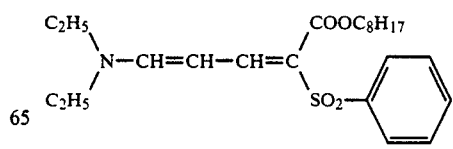

Red mask RM-1

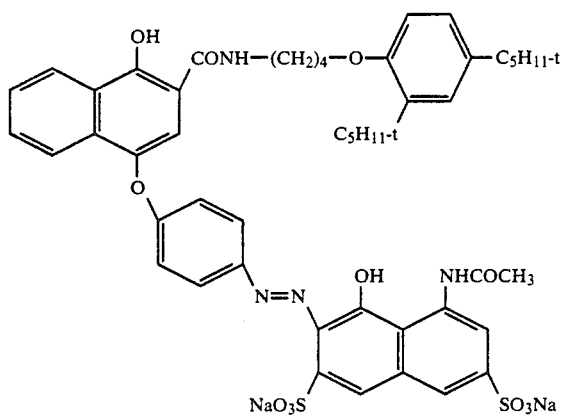

Yellow mask YM-1

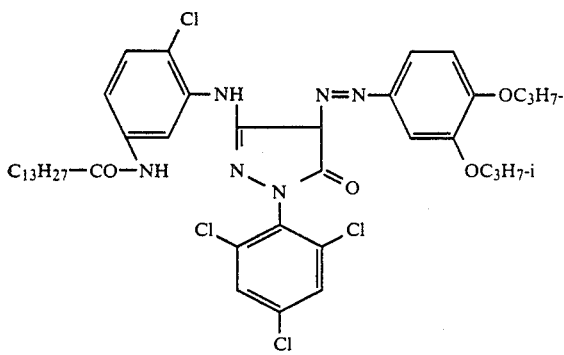

Scavenger SC-1

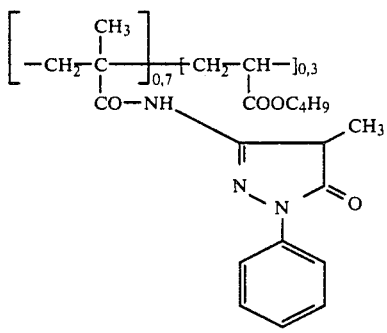

Formaldehyde scavenger FF

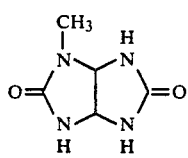

Na perfluorobutane sulfonate is used as wetting agent in all the layers. DIR coupler used in layer combination 1A (comparison):

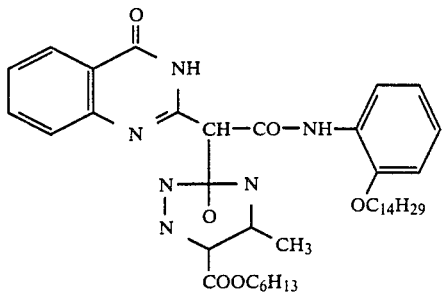
DIR-A

Other layer combinations 1B to 1H were produced in the same way, differing from layer combination 1A soley in the DIR coupler used in layers 3, 5, and 8.

The following DIR couplers were used in layer combinations 1 B, 1 C and 1 D (comparison):

(layer combination 1 B)

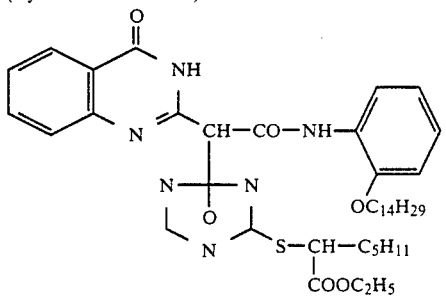
DIR-B (layer combination 1 C)

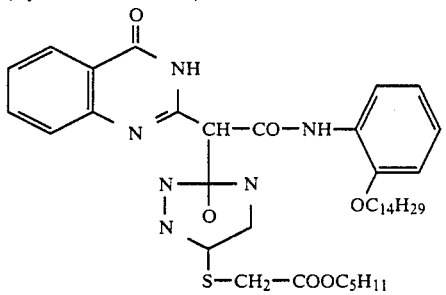
DIR-C (layer combination 1 D)

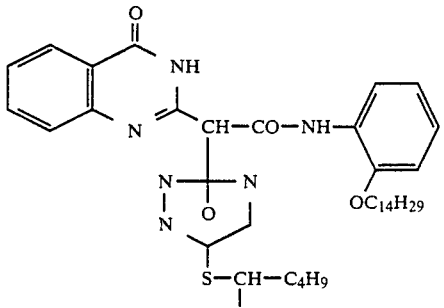
DIR D

DIR couplers according to the invention were used in layer combinations 1 E to 1 H, differing from DIR couplers DIR-A to DIR-D solely in the fact that they contain an o-cyclohexylphenoxy group instead of the tetradecyloxy group.

Development was carried out after exposure of a grey wedge, as described in "The British Journal of Photography", 1974, pages 597 and 598.

The results after processing are shown in Table 1. The inter-image effects IIE are calculated as follows:

$$IIE_{cy} = \frac{\gamma_{red} - \gamma_w}{\gamma_w} \quad ; \quad IIE_{mg} = \frac{\gamma_{green} - \gamma_w}{\gamma_w}$$

$$IIE_{cy} = \frac{\gamma_{blue} - \gamma_w}{\gamma_w} \quad ;$$

where $\gamma_{red}$ is the gradation on selective exposure with red light;
$\gamma_{green}$ is the gradation on selective exposure with green light;
$\gamma_{blue}$ is the gradation on selective exposure with blue light;
$\gamma_w$ is the gradation on exposure with white light.

The edge effect EE shown in Table 1 is the difference between the microdensity and macrodensity for a macrodensity of 1, as described in James, The Theory of the Photographic Process, 4th Edition, Macmillan Publishing Co., Inc. 1977, page 611. In Table 1:
$EE_{cy}$ is the EE in the red-sensitized layer
$EE_{mg}$ is the EE in the green-sensitized layer

TABLE 1

| Layer combination | DIR coupler DIR | [mmol/100 g AgNO₃] | IIE_y | IIE_mg | IIE_cy | KE_mg | KE_cy |
|---|---|---|---|---|---|---|---|
| 1 A | A | 5.0 | | 37 | 40 | 0.49 | 0.62 |
| 1 E | 1 | 5.0 | | 37 | 38 | — | — |
| 1 B | B | 2.7 | 0 | 24 | 32 | 0.20 | 0.31 |
| 1 F | 12 | 2.8 | 1 | 35 | 38 | 0.18 | 0.34 |
| 1 C | C | 3.1 | 5 | 37 | 18 | 0.15 | 0.17 |
| 1 G | 13 | 3.1 | 14 | 82 | 61 | 0.52 | 0.79 |
| 1 D | D | 2.9 | 12 | 36 | 33 | 0.33 | 0.40 |
| 1 H | 14 | 2.9 | 16 | 56 | 32 | 0.44 | 0.56 |

We claim:

1. A color photographic recording material comprising at least one photosensitive silver halide emulsion layer and a DIR coupler associated therewith, characterized in that the DIR coupler corresponds to general formula I:

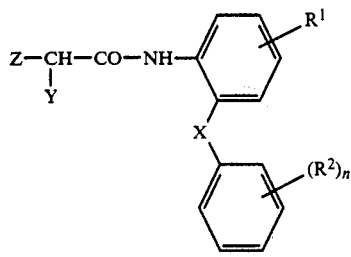

in which
R¹ is H, Cl, —CF₃, alkoxy, sulfamoyl;
R² is H, Cl, alkyl, cycloalkyl, alkoxy, alkoxycarbonyl, carbamoyl;
n is 0, 1 or 2;
X is O or S;
Y is a group with a silver halide development inhibiting function releasable during color development;
Z is benzoyl, carbomoyl or a quinazolin-4-on-2-yl group.

2. A color photographic recording material comprising at least one photosensitive silver halide emulsion layer and a DIR coupler associated therewith, characterized in that the DIR coupler corresponds to general formula I:

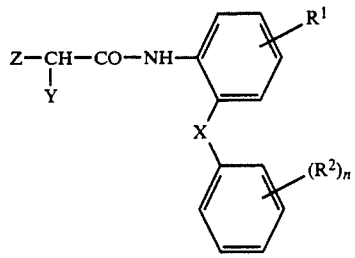

in which
R¹ is H, Cl, —CF₃, alkoxy, sulfamoyl;
R² is H, Cl, alkyl, cycloalkyl, alkoxy, alkoxycarbonyl, carbamoyl;
n is 0, 1 or 2;
X is O or S;
Y is a group with a silver halide development inhibiting function releasable during color development;
Z is a quinazolin-4-on-2-yl group.

3. A color photographic recording material comprising at least one photosensitive silver halide emulsion layer and a DIR coupler associated therewith, characterized in that the DIR coupler corresponds to general formula I:

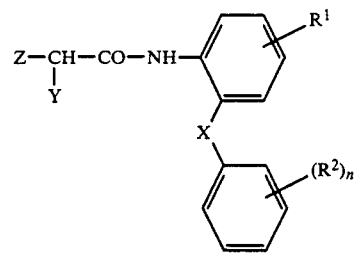

in which
R¹ is H, Cl, —CF₃, alkoxy, sulfamoyl;
R² is an o-cyclohexyl group;
X is O or S;
Y is a group with a silver halide development inhibiting function releasable during color development;
Z is a quinazolin-4-on-2-yl group.

4. A color photographic recording material as claimed in claim 1 wherein R² is an o-cyclohexyl group.

5. The color photographic recording material as claimed in claim 2 wherein Y is a 1,2,3-triazole or a 1,2,4-triazole.